(12) United States Patent
Sun

(10) Patent No.: US 6,339,183 B1
(45) Date of Patent: *Jan. 15, 2002

(54) TRANSGENIC MAMMALS EXPRESSING HETEROLOGOUS DNA IN UROTHELIUM AND ISOLATION OF BIOLOGICALLY ACTIVE MOLECULES FROM URINE

(75) Inventor: Tung-Tien Sun, Scarsdale, NY (US)

(73) Assignee: New York University, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/969,315

(22) Filed: Nov. 13, 1997

Related U.S. Application Data

(63) Continuation-in-part of application No. 08/907,800, filed on Aug. 8, 1997, now Pat. No. 6,001,646, which is a continuation-in-part of application No. 08/464,961, filed on Jun. 5, 1995, now Pat. No. 5,824,543.

(51) Int. Cl.[7] ........................ A01K 67/027; C12P 21/00; C12N 15/00
(52) U.S. Cl. ................... 800/14; 800/4; 800/15; 800/16; 800/17; 800/18; 435/320.1
(58) Field of Search ................... 800/18, 4, 10, 800/13, 14, 15, 16, 17; 435/455, 462, 463, 69.1, 320.1

(56) References Cited

U.S. PATENT DOCUMENTS 4,873,191 A 10/1989 Wagner et al. ............ 435/172.3

OTHER PUBLICATIONS

Mullins et al. Journal of Clinical Investigations, vol. 98, No. 11, pp. S37–S40, 1996.*
Jaenisch, Science, vol. 240, pp. 1468–1474, Jun. 10, 1988.*
Houdebine, Journal of Biotechnology, vol. 34, pp. 269–287, 1994.*
Kappel et al., Current Opinion in Biotechnology, vol. 3, pp. 548–553, 1992.*
Wall, Theriogenology, vol. 45, pp. 57–68, 1996.*
Srojek & Wagner, Genetic Engineering: Principles and Methods, vol. 10, pp. 221–246, 1988.*
Ebert et al., Molecular Endocrinology, vol. 2, pp. 277–283, 1988.*
Hammer et al., Journal of Animal Science, vol. 68, pp. 269–278, 1988.*
Wu et al., "Mammalian Uroplakins a Group of Highly Conserved Urothelial Differentiation–Related Membrane Proteins", The Journal of Biological Chemistry, 269(18): 13716–13724 (1994).*
Bishop and Smith, "Mechanism of Chromosomal Integration of Microinjected DNA", Molecular Biology Medicine 1989, 6, 283–298.
Chu et al., "Electroporation for the efficient transfection of mammalian cells with DNA", Nucleic Acids Research 1987, 15, 1311–1326.
Diatchenko et al. "Suppression subtractive hybridization: A method for generating differentially regulated or tissue–specific cDNA probes and libraries", Proc. Nat'l Acad. Sci. 1996, 93, 6025–6030.
Frohman et al. "Rapid production of full–length cDNAs from rare transcripts: Amplification using a single gene–specific oligonucleotide primer", Proc. Nat'l Acad. Sci. USA 1988, 85, 8998–9002.
Gordon et al. "Genetic transformation of mouse embryos by microinjection of purified DNA", Proc. Natl. Acad. Sci. USA 1980, 77, 7380–7384.
Gordon and Ruttel, "Gene Transfer into Mouse Embryos: Production of Transgenic Mice by Pronuclear Injection", Methods in Enzymology 1983, 101, 411–433.
Graham and Van der Ebb, "A New Technique for the Assay of Infectivity of Human Adenovirus 5 DNA", Virology 1973, 52, 456–467.
Hicks, R.M. "The Fine Structure of the Transitional Epithelium of Rat Ureter", J. Cell Biol. 1965, 26, 25–48.
Hicks, R.M. "The Mammalian Urinary Bladder: An Accommodating Organ", Biol. Rev. 1975, 50, 215–246.
Jaenisch et al., "Chromosomal Position and Activation of Retroviral Genomes Inserted into the Germ Line of Mice", Cell 1981, 24, 519.
Koss, L.G. "The Asymmetric Unit Membranes of the Epithelium of the Urinary Bladder of the Rat", Lab. Invest. 1969, 21, 154–168.
Lin et al. "Precursor Sequence Processing, and Urothelium–specific Expression of a Major 15–kDa Protein Subunit of Asymmetric Unit Membrane", J. Biol. Chem. 1994, 269, 1775–1784.
Mercer et al. "The Dopamine β–Hydroxylase Gene Promoter Directs Expression of E. coli lacZ to Sympathetic and Other Neurons in Adult Transgenic Mice", Neuron 1991, 7, 703–716.
Perucho et al., "Genetic and Physical Linkage of Exogenous Sequences in Transformed Cells", Cell 1980, 22, 9–17.

(List continued on next page.)

Primary Examiner—Deborah Crouch
(74) Attorney, Agent, or Firm—Browdy And Neimark

(57) ABSTRACT

A vector is provided which contains a promoter construct linked to a heterologous gene encoding a selected biologically active molecule or oncogene wherein the promoter construct is capable of directing urothelial expression of the heterologous gene. Methods of isolating biologically active molecules from urine of animals transfected with this vector and transgenic animals containing this vector are also provided.

8 Claims, 5 Drawing Sheets

OTHER PUBLICATIONS

Peschon et al. "Spermatid–specific expression of protamine 1 in transgenic mice", *Proc. Natl. Acad. Sci. USA* 1987, 84, 5316–5319.

Ryan et al. "Chromosomal localization of uroplakin genes of cattle and mice", *Mamm. Genome* 1993, 4, 656–661.

Soriano et al. "Tissue–Specific and Ectopic Expression of Genes Introduced into Transgenic Mice by Retroviruses", *Science* 1986, 234, 1409–1413.

Stewart et al. "Expression of retroviral vectores in transgenic mice obtained by embryo infection", *Embo. J.* 1987, 6, 383–388.

Staehelin, L.A. "Lumenal Plasma Membrane of the Urinary Bladder", *J. Cell Biol.* 1972, 53, 73–91.

Wu et al. "Large Scale Purification and Immunolocalization of Bovine Uroplakins I, II, and III", *J. Biol. Chem.* 1990, 265, 19170–19179.

Wu et al. "Uroplakins Ia and Ib, Major Differentiation Products of Bladder Epithelium, Belong to a Family of Four Transmembrane Domain (4TM) Proteins", *J. Biol. Chem.* 1994, 269, 13716–13724.

Wu, X.–R. and Sun, T.–T. "Molecular cloning of a 47 kDa tissue–specific and differentiation–dependent urothelial cell surface glyprotein", *J. Cell Sci.* 1993, 106, 31–43.

Yu et al., "Uroplakin I: A 27–kD Protein Associated with the Assymmetric Unit Membrane of Mammalian Urothelium", *J. Cell Biol.* 1990, 111, 1207–1216.

Yu et al., "Identification of an 85–100 kDa Glycoprotein as a Cell Surface Marker for an Advanced Stage of Urothelial Differentiation: Association with the Inter–plaque ('Hinge') Area", *Epithelial Cell Biol.* 1992, 1, 4–12.

Yu, J. "Uroplakin I: A 27–kD Protein Associated with the Asymmetric Unit Membrane of Mammalian Urothelium", *J. Cell Biol.* 1994, 125, 171–182.

* cited by examiner

TRANSGENIC MAMMALS EXPRESSING HETEROLOGOUS DNA IN UROTHELIUM AND ISOLATION OF BIOLOGICALLY ACTIVE MOLECULES FROM URINE

CROSS-REFERENCE TO RELATED APPLICATIONS

This application is a continuation-in-part of U.S. application Ser. No. 08/907,800, filed Aug. 8, 1997, now issued as U.S. Pat. No. 6,001,646, which is a continuation-in-part of U.S. application Ser. No. 08/464,961 filed Jun. 5, 1995 now issued as U.S. Pat. No. 5,824,543.

BACKGROUND OF THE INVENTION

Methods of producing biologically active molecules by transfer of recombinant genes into cell in culture and into live animals have been developed. For example, DNA molecules have been introduced into cultured cells by calcium phosphate precipitation or electroporations. Graham and Van der Ebb *Virology* 1973, 52, 456–467; Perucho et al. *Cell* 1980, 22, 9–17; Chu et al. *Nucleic Acids Research* 1987, 15, 1311–1326; and Bishop and Smith *Molecular Biology Medicine* 1989, 6, 283–298. DNA molecules have also been introduced into the nucleus of cells in culture by direct microinjection. Gordon et al. *Proc. Natl Acad. Sci. USA* 1980, 77, 7380–7384; Gordon and Ruttel *Methods in Enzymology* 1983, 101, 411–433; and U.S. Pat. No. 4,873,191.

However, there are two major problems of producing biologically active molecules such as protein products on a commercially viable scale via these methods. First, bacterial expression systems frequently fail to modify the proteins properly, i.e., by glycosylation, etc. Second, the subsequent isolation of gene products from the expression systems can be extremely difficult. In bacteria, yeast, and baculovirus systems the expressed proteins are most often purified from insoluble intracellular compartments. Secreted proteins in yeast require specialized protease-deficient strains coupled with appropriate vectors with secretion signals.

Retroviral vectors have also been used to introduce DNA molecules into the genome of animals. Jaenisch et al. *Cell* 1981, 24, 519; Soriano et al. *Science* 1986, 234, 1409–1413; and Stewart et al. *Embo. J.* 1987, 6, 383–388. Recombinant genes have been introduced into primary cultures of bone marrow, skin, fibroblasts, or hepatic or pancreatic cells and then transplanted into live animals. There has also been success in using mammary gland-specific promoters to drive the expression of foreign proteins in these secretory glands, ultimately leading to their secretion in the resultant milk. This method has been used commercially to express human growth hormone in cows and sheep. WO 94/05782. The copious volumes of milk produced by cows and sheep make this procedure attractive. However, this method suffers from several potential drawbacks: one being that the expressed protein even at relatively high levels must be purified away from a large amount of milk proteins such as caseins, immunoglobins, lactoferrins which may also entrap the desired valuable product; another being that certain protein products may be insoluble in the calcium-rich environment of milk fluid; and another being that this method requires the use of pregnant animals which are expensive and time consuming to produce.

SUMMARY OF THE INVENTION

An object of the present invention is to provide a vector comprising a promoter construct capable of directing urothelial gene expression of a heterologous gene encoding a selected biologically active molecule linked thereto. The vectors of the present invention are useful in directing the expression of the heterologous gene in urothelial cells transfected with the vector which then secrete the encoded gene product into the urine for isolation, thus transforming the bladder into a bioreactor.

Accordingly, another object of the present invention is to provide a method of producing a selected biologically active molecule in urine of an animal wherein urothelial cells in the animal are transfected with the vector so that the heterologous gene of the DNA sequence is expressed and the selected biologically active molecule is recovered in urine produced by the animal.

Another object of the present invention is to provide nonhuman transgenic animals produced using this vector.

Another object of the present invention is to provide animal models for human bladder cancer.

BRIEF DESCRIPTION OF THE FIGURES

FIGS. 1a and 1b show the organization and nucleotide sequence of the mouse uroplakin II (UPII) genomic DNA. FIG. 1a provides the exon-intron organization of mouse UPII gene. The open and filled thick boxes denote the five coding sequences (exons) and non-coding sequences (introns), respectively, of the gene. The open and filled thin boxes represent a $(CA)_n$ dinucleotide repeat region and an Alu-like murine B1 repeat, respectively. G1 and G2 designate two independent and partially overlapping genomic clones. The restriction sites are SacI (S), NcoI (N), BamHI (B), SalI (Sal), and XhoI (X). FIGS. 1b-1 and 1b-2 provide the nucleotide sequence (SEQ ID NO: 1) of a 4-kb SacI fragment of mouse UPII gene. A reversed B1 repetitive sequence (in the 5' upstream region) and a potential polyadenylation site (AATAAA; in the 3' untranslated region) are underlined and double-underlined, respectively. The wavy arrow denotes the transcriptional initiation site. Broken arrows marked 1 to 4 denote the intron/exon junctions of the four introns. The predicted first amino acid residue of mature UPII protein sequence is marked with an asterisk. The preceding domain contains a pre and a pro sequence of 25 and 59 amino acids, respectively.

FIG. 2 illustrates the tissue distribution of UPII mRNA as assayed by RT-PCR. Poly(A)+ mRNAs (0.3–0.4 mg) from mouse bladder (lanes 1 and 13), skin (2), forestomach (3), glandular stomach (4), kidney (without renal pelvis) (5), liver (6), spleen (7), testis (8), and thalamus/hypothalamus (9), cerebral cortex (10), and cerebellum (11) regions of the brain were reverse-transcribed, and amplified with either UPII-specific primers (Upper; 266 bp) or glyceraldehyde-3-phosphate dehydrogenase (GDH)-specific primers (Lower, as an internal control for comparison; 130 bp). The PCR products were then electrophoresed on a 1.3% agarose gel and stained with ethidium bromide. Lane 12 is a negative control (no cDNA template). The 266-bp UPII product was detected in abundance in bladder, but not in any other tested tissues, including the hypothalamus.

FIG. 3a provides a restriction map (abbreviations as described in FIG. 1) of the endogenous murine UPII gene. A 500-bp PCR fragment (thick bar) was used as a probe which detects a 1.4-kb NcoI fragment of the endogenous UPII genome but a shorter 1.1-kb NcoI fragment of the transgene. FIG. 3b provides restriction map of the transgene. A 3.6-kb 5'-flanking sequence of the UPII gene was inserted into an *Escherichia* coli β-galactosidase (β-gal)-encoding placF vector. In this particular test expression vector, a sequence containing a part of exon 1 and all of intron 1 and exon 2 of the mouse protamine-1 gene (mp1) was placed at the 3'-end of the β-gal (or lacZ) gene to provide an exon/intron splicing site and a polyadenylation signal. This chimeric gene was cut out from the vector, gel-purified, and microinjected into mouse eggs.

DETAILED DESCRIPTION OF THE INVENTION

Figure 1A:
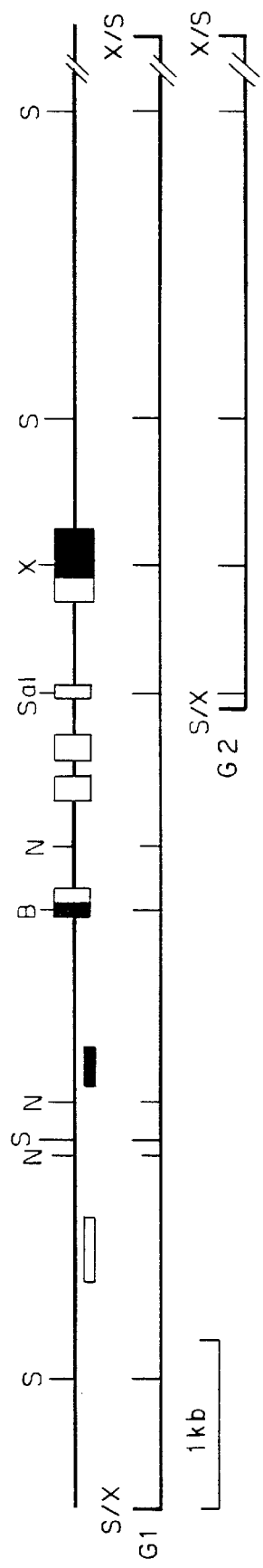

Urine in the bladder is of relatively high osmolality (50 to 1,000 mosmol/kg), with pH values as low as 4.5 and high concentrations of urea and ammonium. The lumen of the bladder therefore provides an advantageous environment for the production of proteins that are normally difficult to express due to insolubility. The urea and high osmolality may serve as in situ denaturants and chaotropic agents. However, urine contains relatively little protein, in comparison with milk, as the kidneys are designed to prevent protein loss, therefore urothelial promoter-driven expression of proteins which by-passes the kidney produces the desired protein in a solution with relatively little contaminating host endogenous proteins.

In the present invention, a vector and method have been developed for expressing biologically active molecules in the luminal cavity of the bladder of transgenic mammals.

The vector of the present invention comprises a promoter construct capable of directing urothelial gene expression of a heterologous gene encoding a selected biologically active molecule linked to the promoter construct. Promoters active in directing expression in the urothelium can be routinely identified in accordance with the teachings provided herein and used in the promoter construct of the vectors of the present invention.

Urothelium, also known as transitional epithelium, is a multilayered epithelium that covers the surface of much of the urogenital tract including the renal pelvis, ureter, the entire bladder and a portion of the urethra. The apical surface of urothelium, in direct contact with the urine, is covered with numerous rigid looking plaques. These plaques cover a large portion of the apical surface of mammalian urothelium. Hicks, R. M. *J. Cell Biol.* 1965, 26, 25–48; Koss, L. G. *Lab. Invest.* 1969, 21, 154–168; Staehelin, L. A. *J. Cell Biol.* 1972, 53, 73–91. They are believed to play a crucial role as a permeability barrier (Hicks, R. M. *Biol. Rev.* 1975, 50, 215–246) and/or as physical stabilizer of the urothelial cell surface (Staehelin, L. A. *J. Cell Biol.* 1972, 53, 73–91). When viewed in cross section, the outer leaflet of the plaque is almost twice as thick as the inner one, hence the term "asymmetrical unit membrane" or "AUM" has been used to describe these plaques.

It has recently been shown that AUM contain 4 major integral membrane proteins which are called uroplakin Ia (UPIa; 28 kDa), uroplakin Ib (UPIb; ~27 kDa), uroplakin II (UPII; 15 and uroplakin III (UPIII; 47 kDa). EM-immunolocalization studies established that these uroplakins are AUM-associated in situ, thus establishing them as the major protein subunits of urothelial plaques. Yu et al. *J. Cell Biol.* 1990, 111, 1207–1216; Wu et al. *J. Biol. Chem.* 1990, 265, 19170–19179. Immunohistochemical survey of various bovine tissues established that these UPs are urothelium-specific being present in the upper cell layers of the urothelia that cover the urogenital tract including the renal pelvis, ureter, bladder and part of the urethra. These data established uroplakins as excellent markers for an advanced stage of urothelia differentiation. Yu et al. *J. Cell Biol.* 1990, 111, 1207–1216; Wu et al. *J. Biol. Chem.* 1990, 265, 19170–19179. Furthermore, uroplakins Ia, Ib, II and III appear to be the major protein components of all mammalian urothelial plaques. They are found in eight other mammalian species (human, monkey, sheep, pig, dog, rabbit, rat, and mouse), and the AUMs of these species appear morphologically similar, bearing crystalline patches of 12-nm protein particles with a center-to-center spacing of 16.5 nm. Wu et al. *J. Biol. Chem.* 1994, 269, 13716–13724.

The primary structures of UPs have recently been elucidated by cDNA cloning. The results established the existence of two closely related UPI isoforms, the 27-kDa UPIa and the 28-kDa UPIb. Yu, J. *J. Cell Biol.* 1994, 125, 171–182. The mRNAs of all four known UPs have recently been shown to be urothelium-specific, indicating that expression of UP genes is transcriptionally regulated. Yu, J. *J. Cell Biol.* 1994, 125, 171–182; Lin et al. *J. Biol. Chem.* 1994, 269, 1775–1784; Wu, X.-R. and Sun, T.-T. *J. Cell Sci.* 1993, 106, 31–43.

The expression of the mouse UPII gene, like its bovine counterpart, is urothelium- and late-differentiation stage-specific. Using transgenic mouse techniques, a 3.6-kb 5' flanking region has now been identified as a promoter comprising the cis-elements for directing the expression of a heterologous reporter gene specifically and efficiently to the suprabasal cell layers of the urothelium in a manner similar to the endogenous UPII gene. Using this promoter, it has now been found that foreign proteins can be directed to the upper cell layer of the bladder urothelium for expression and secretion into urine.

Figure 1B-1:
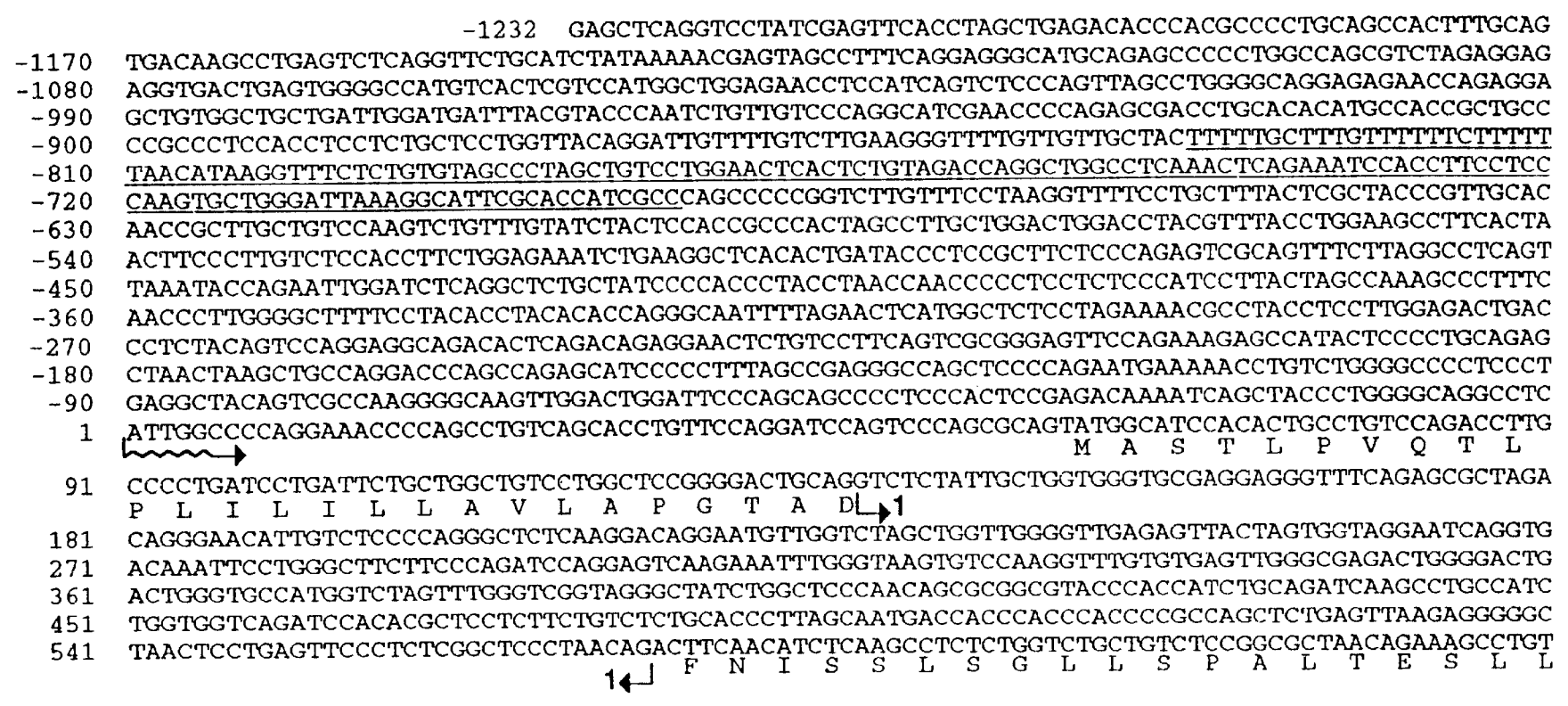
Figure 1B-2:
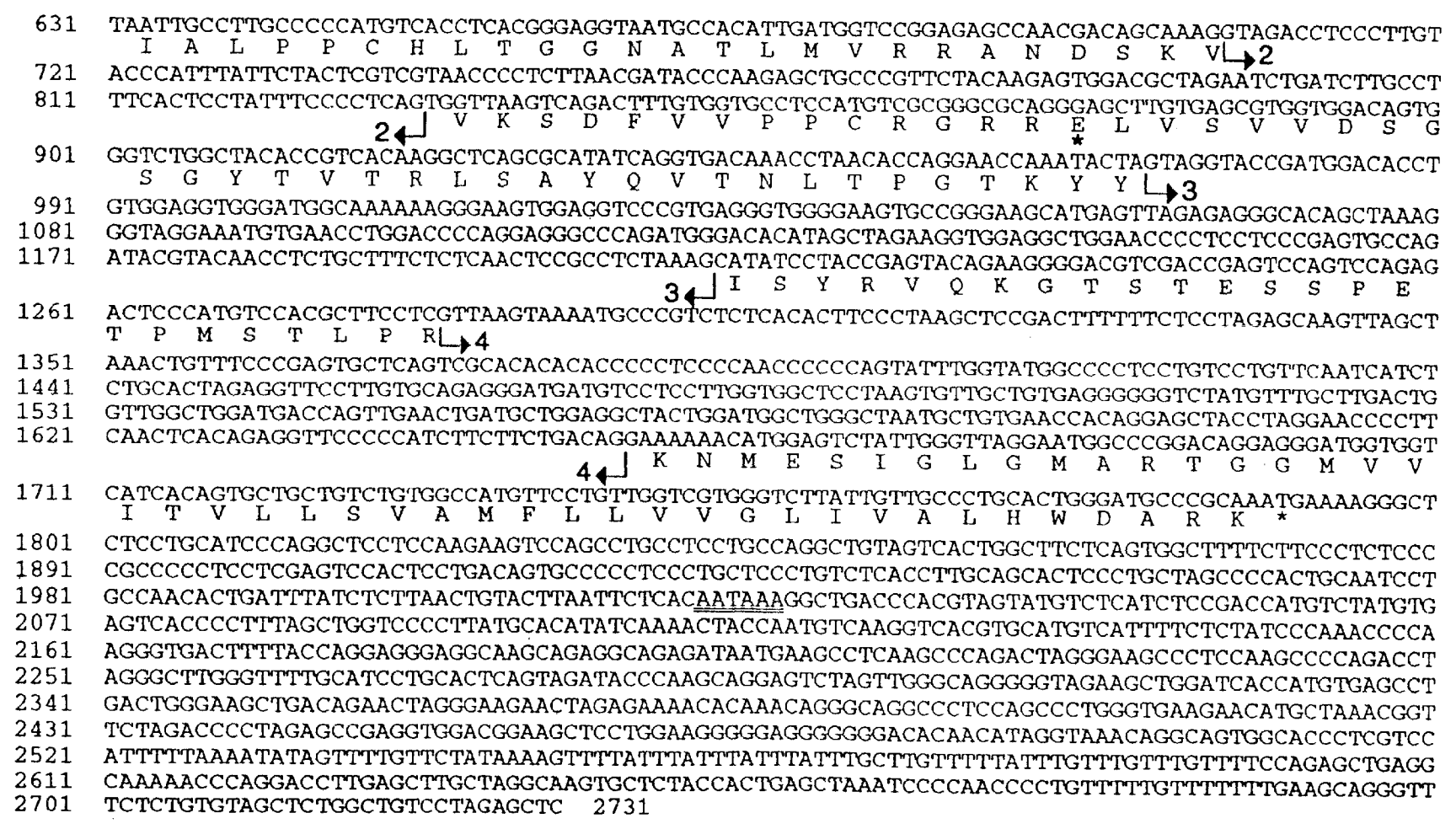

Using a bovine UPII CDNA as a probe, a 16-kb mouse genomic clone (G1) was isolated which contains an ~2.5-kb transcribed region that is flanked by ~3.5-kb and ~10 kb of 5'- and 3'- sequences, respectively (see FIG. 1a). Alignment of the coding sequence with the UPII cDNA sequences of cattle (Lin et al. *J. Biol. Chem.* 1994, 269, 1775–1784), which are highly homologous, defined the exon/intron junctions of four introns (FIG. 1b). 5'-RACE (Frohman et al. *Proc. Nat'l Acad. Sci. USA* 1988, 85, 8998–9002) experiments using mouse bladder mucosal mRNA as a template established that the transcription site of the UPII gene is located at 60-bp 5'-upstream of the translation initiation codon and 27-bp downstream of a putative TATA box. The 5'-upstream region contains an Alu-like B1 repetitive sequence (–830 bp) and a $(CA)_n$ stretch (~–2.1 kb). Finally, a polyadenylation signal resides ~230 bp downstream of the translation stop codon (see FIG. 1b).

Figure 2:
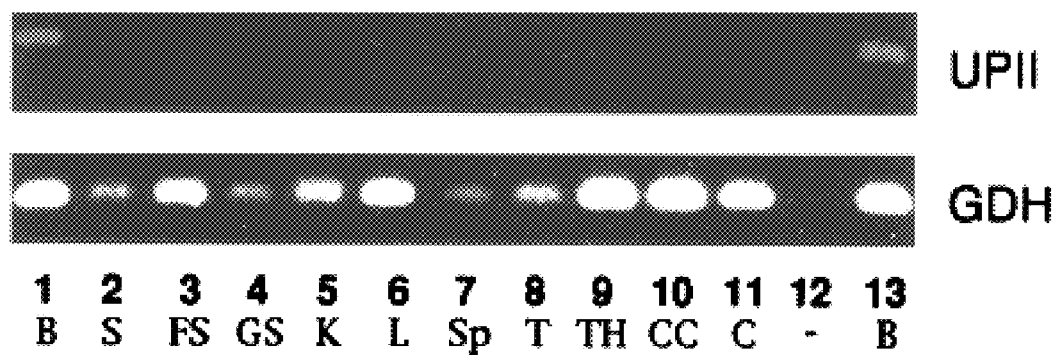

The mouse UPII gene is also expressed in the urothelium. mRNAs were prepared from various mouse tissues and probed for the presence of UPII sequences by reverse transcription-polymerase chain reaction (RT-PCR) assay. A large amount of UPII product of expected size (266-bp) was generated from the bladder, but not from skin, forestomach, glandular stomach, kidney, liver, spleen, testis, or the hypothalamus/thalamus cortex and cerebellum of the brain (see FIG. 2).

A rabbit antiserum previously prepared against a synthetic peptide corresponding to the N-terminal amino acid sequence ELVSVVDSGSG (1–11) (SEQ ID NO: 2) of mature bovine UPII (Lin et al. *J. Biol. Chem.* 1994, 269, 1775–1784) immunohistochemically stains the 15-kDa bovine UPII and localizes it to the superficial cell layers of bovine urothelium. This antiserum cross-reacted well with mouse UPII, which contains an identical epitope, but migrates slightly slower at an apparent 17 kDa mass. Immunofluorescent staining of frozen sections of mouse bladders showed that the UPII was associated with the all the suprabasal cell layers, suggesting that the onset of UPII gene expression in mouse was earlier than that in cattle.

Figure 3A:
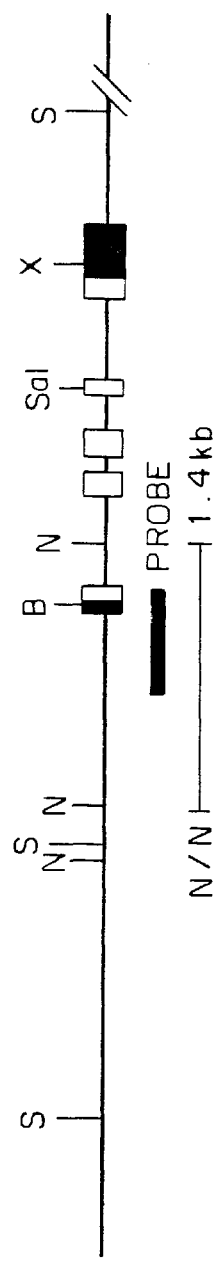
FIGS. 3a and 3b illustrate the construction and quantitation of a representative transgene.
Figure 3B:
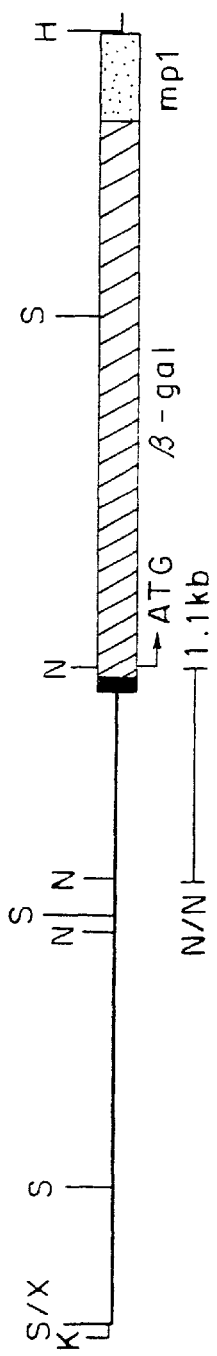

To define the cis promoter elements for urothelial-specific expression and to demonstrate that heterologous genes can be targeted to the suprabasal urothelial cells as endogenous UPII, a transgenic mouse was constructed that contains a chimeric gene in which a lacZ reporter gene was under the regulation of a 3.6-kb 5'-flanking sequence of the mouse UPII gene (FIG. 3b). The DNA construct was injected into fertilized mouse eggs for transgenic mouse production. Southern blot analyses of the tail DNAs showed that the transgene was integrated into the genomes of 4 of 25 mice. Three of these animals transmitted the reporter gene into their progeny. Southern blot analyses established that the genomic DNAs of these three transgenic lines, TG1, TC2, and TG3, contained roughly 40, 6, and 30 copies, respectively, of the reporter gene per diploid genome. Probing the same Southern blot with the lacZ sequence showed that the transgene of all three lines were in tandem repeats and were integrated into independent sites.

In all three mice lines, the transgene was expressed in the suprabasal cells of the bladder epithelium in an expression pattern similar to the endogenous UPII gene. The staining correlated somewhat with gene dosage, as it was intense in TG1 (40 copies) but moderate in TG2 (6 copies) and TG3 (30 copies). β-galactosidase activity was only observed in the bladder and other urothelia of mice that had inherited the transgene, confirming that the activity was transgene-specific. In all three transgenic mice, no β-galactosidase activity was detected in any of the non-urothelial stratified epithelia tested, including those of the skin, tongue, cornea, esophagus, and forestomach. The reporter gene product was also undetectable in all other epithelia tested, including those of liver, lung, glandular stomach, small and large intestine, uterus, and testis; or mesenchymal tissues, including fibroblasts, endothelial cells, spleen, and various muscle cells.

Experiments have also been performed wherein uroplakin II promoter was used to drive the expression of the biologically active human growth hormone gene in the urothelium of transgenic mice. In these experiments, a vector was constructed with the 3.6-kb UPII promoter placed upstream from a human growth hormone cDNA. The vector was then injected into the fertilized mouse eggs for transgenic mouse production. Thirteen founder mice were generated. Of these, six (5 male and 1 female) transmitted the transgene to their offspring. Immunofluorescence staining of the bladder epithelium of these transgenic mine using antibodies to hGH showed strong staining indicating high level of expression. Immunolocalization performed by high resolution electron microscopy showed the accumulation of electron dense, aggregates of hGH that are labeled by immuno gold particles conjugated with antibodies to hGH. Most of the hGH particles are found in the vesicles lined with the asymmetrical unit membrane that are normally involved in transporting the uroplakins to the apical surface of the bladder epithelium. In addition, some of the hGH particles formed another distinct population of cytoplasmic vesicles thus revealing the presence of a previously unrecognized secretory pathway that may normally operate at a low level in bladder epithelium. The high level of overexpression of hGH makes these vesicles easily visible.

Urine from these mice was collected and hormone levels determined by radioimmunoassay. Many of the F1 offspring had a significant levels of the human growth hormone in their urine (up to 300 ng/ml) thus demonstrating that the biologically active molecule was secreted into the urine. Further, blood concentrations of the hormone were less than 5 ng/ml indicating that the synthesized hormone is secreted vectorially into the bladder cavity rather than into the bloodstream.

Other urothelia closely related to the epithelium of the bladder known to cover other areas of the urinary tract, such as the renal pelvis of the kidney, the ureter, and the urethra and which also elaborate AUM plaques, exhibit similar expression of the transgene.

These data show that a promoter active in directing expression in the urothelium of an animal, such as the 3.6-kb 5'-flanking sequence of the mouse UPII gene, can drive both a heterologous reporter gene and a gene for a biologically active molecule to express in the upper cell layers of the bladder epithelium. The lack of expression in non-urothelial tissues indicates a high degree of tissue-specificity and demonstrates that the cis elements of this promoter region provide very tight regulatory control on tissue-specific and differentiation-dependent expression of a gene placed downstream of the promoter. As these results were corroborated in independcent transgenic lines with differing sites of transgene integration, they show that the inherent promoter activity is responsible for the tissue-specific expression and is not due to the effect of neighboring sequences of the transgene integration sites. This tight regulation is a very desirable property of any promoter used for production of foreign protein products in host transgenic animals, as it assures correct delivery to target production sites, high efficiency of expression of transduced genes, and minimizes toxic effect of aberrant expression.

It has also been found that a urothelium specific promoter can direct expression of a human oncogene to the urothelium and is useful in the production of animal models for human bladder cancer. In these experiments, a chimeric gene comprising a 3.6 kb 5'-flanking sequence of mouse uroplakin II gene and a 2.8 kb SV40 large T oncogene was constructed. This chimeric gene was then microinjected into fertilized mouse eggs which were implanted into foster mothers to produce transgenic mice expressing the oncogene. Four transgenic founder mice carrying uroplakin II/SV40 large T chimeric genes were identified from thirty live births. Two of these positive founder mice harboring 10 and 6 copies of transgenes succumbed with bladder tumors at ages of 3 and 5 months, respectively. Histological examination revealed tumors were invasive transitional cell carcinomas, resembling those occurring in humans. Reverse transcriptase polymerase chain reaction confirmed the expression of SV40 large T oncogene in urothelial tumors, but not in non-urothelial, normal tissues. Immunohistochemical staining showed the typical nuclear staining of SV40 large T antigen in bladder tumor cells. The remaining two transgenic mice carried lower copy number of transgenes and exhibited a urothelial morphology resembling carcinoma in situ as is seen in humans. In contrast, no tumors were seen in over 50 transgene negative mice.

While all of the experiments discussed above were conducted using the mouse UPII promoter, as will be obvious to those of skill in the art upon this disclosure, other promoter constructs capable of directing urothelial gene expression can used to yield similar results. For example, mouse uroplakin II 5'-upstream sequences that are shorter or longer than 3.6-kb but can still achieve the same degree of urothelium expression. Also useful are DNA sequences with relatively minor modifications to the mouse UPII promoter, such as sequences with point mutations, partial deletions or chemical modifications.

In addition, sequences that are related to the 3.6 kb 5' flanking sequence of the mouse uroplakin gene, including, but not limited to, promoter sequences of uroplakin-II-homologous genes of other mammalian species such as human, cattle, sheep, goat, rabbit and rat, can also be used. There is sufficient similarity between this gene in different species, so that similar results with the UPII promoter sequence in other animals is expected. For example, the UP gene organization (Ryan et al. *Mamm. Genome* 1993, 4, 656–661), cDNA (Lin et al. *J. Biol. Chem.* 1994, 269, 1775–1784) and protein sequences, tissue patterns of expression, and morphology of AUMs are strikingly similar between the mouse and cow. The amino acid sequence of bovine and mouse UPII are highly similar, sharing 84 of their 100 amino acid residues. Wu et al. *J. Biol. Chem.* 1994, 269, 13716–13724. In addition, although the onset of expression of the UPII gene is different in these two species, UPII is clearly differentiation-related in both cow and mouse urothelia.

Further, promoters of other genes that are active in directing expression in the urothelium are known and can also be used in the vectors of the present invention. Examples include, but are not limited to, the promoter of uroplakin 1a (Yu et al. *J. Cell Biol.* 1994, 125, 171–182; Yu et al. *J. Cell Biol.* 1990, 111:1207–16), uroplakin Ib (Yu et al. *J. Cell Biol.* 1994, 125, 171–182; Yu et al. *J. Cell Biol.* 1990, 111:1207–16), uroplakin III (Wu, X. R., and Sun, T. T. *J. of Cell Science* 1993, 106, 31–43, and the urohingin gene (Yu et al. *Epithelial Cell Biol.* 1992, 1, 4–12).

Identification of additional promoters active in directing gene expression in the urothelium is performed routinely using the subtraction library technique. Using this technique which eliminates the cDNAs that are shared by multiple tissues (Diatchenko et al. *Proc. Nat'l Acad. Sci.* 1996, 93, 6025–6030), a library highly enriched in bladder specific cDNAs was generated. Total RNAs were isolated from bovine bladder, kidney, lung, spleen, muscle, esophagus, stomach, intestine, colon, liver and brain. Northern blot analysis of these mRNAs using an actin cDNA as a probe demonstrated the intactness of the actin mRNA in all of these preparations. Bladder cDNAs were then used as the "tester", and the cDNAs of all the other non-bladder tissues, referred to as the "drivers" were subtracted from the bladder cDNAs. The cDNAs of the non-subtracted and the subtracted were probed using actin cDNA or uroplakin Ib. The results indicate that the original bovine bladder cDNA preparation contained abundant actin mRNA and relatively little uroplakin Ib mRNA. In contrast, the subtracted library contained almost no detectable actin mRNA (at least 50 fold reduction) but greatly increased uroplakin Ib mRNA (>10 to 15 fold enrichment). Multiple cDNA clones have been isolated from the substraction library and used to probe the mRNAs of various bovine tissues. For example, a uroplakin Ib probe confirmed its bladder specificity. Tissue distribution patterns have also been determined for three unidentified partial cDNAs which are relatively bladder specific. Sequencing data indicate these three clones are novel genes not described previously. It is believed that the promoters of these genes will also be useful in directing expression of a heterologous gene for a biologically active molecule in the urothelium of transgenic animals.

The vectors of the present invention are thus useful in transforming the bladder into a bioreactor capable of producing a biologically active molecule in the urine for isolation. In one embodiment, this vector is introduced into germ cells to produce a transgenic animal capable of expressing the biologically active molecule in its bladder. As used herein, "biologically active molecule" refers to a molecule capable of causing some effect within an animal, not necessarily within the animal having the transgene. Examples of such molecules include, but are not limited to, adipokinin, adrenocorticotropin, blood clotting factors, chorionic gonadotropin, corticoliberin, corticotropin, cystic fibrosis transmembrane conductance regulators, erythropoietin, folliberin, follitropin, glucagon gonadoliberin, gonadotropin, human growth hormone, hypophysiotropic hormone, insulin, lipotropin, luteinizing hormone-releasing hormone, luteotropin, melanotropin, parathormone, parotin, prolactin, prolactoliberin, prolactostatin, somatoliberin, somatotropin, thyrotropin, tissue-type plasminogen activator, and vasopressin. Of course, as will be obvious to one of skill in the art, the above list is not exhaustive. In addition, new genes for biologically active molecules that will function in the context of the present invention are continually being identified. The biologically active molecule can be isolated from the urine of these transgenic animals. Accordingly, the present invention provides a means for isolating large amounts of biologically active molecules from the urine of transgenic animals which can be used for a variety of different purposes.

The vectors of the present invention have also been demonstrated to useful in directing expression of human oncogenes to the urothelia in of transgenic animals. In this embodiment, the vector is introduced into germ cells to produce transgenic animal which serves a model for human bladder cancer.

In another embodiment, the vector comprises a system which is well received by the urothelial cells lining the lumen of the bladder. An example of a useful vector system is the Myogenic Vector System (Vector Therapeutics Inc. Houston Tex.). In this embodiment, the heterologous gene of the biologically active molecule linked to the promoter construct capable of directing urothelial expression and carried in the vector is introduced into the bladder of an animal in vivo. Introduction of the vector can be carried by a number of different methods routine to those of skill in the art. For example, a vector of the present invention could be placed in direct contact with the urothelium via a rubber urethral catheter or Foley catheter. Vectors of the present invention can also be incorporated into liposomes and introduced into the animal in that form. The transgene is absorbed into one or more epithelial cells capable of expressing and secreting the biologically active molecule into the urine collecting in the bladder. It may be preferred for some biologically active molecules to also engineer a signaling sequence into the vector to insure that the molecule is secreted from the apical surface into the lumen. Use of signaling sequences such as the glycophosphatidylinositol (GPI) linkage in anchoring molecules to a selected surface is well known in the art. The biologically active molecule is then voided from the lumen where it can be collected and separated from other components in the urine.

The following nonlimiting examples are provided to further illustrate the present invention.

EXAMPLES

Example 1

Characterization of the Mouse UPII Gene

A bovine UPII cDNA (Lin et al., *J. Biol. Chem.* 1994, 269, 1775–1784) was used as a probe to screen a mouse EMBL3-SP6A/T7 genomic library (Clontech Laboratories Inc., Palo Alto, Calif.). Two overlapping clones (G1 and G2) were isolated (FIG. 1*a*) and were sequenced by the dideoxynucleotide termination method. The transcriptional initiation site was determined by sequencing three clones of 5'-RACE (rapid amplification of cDNA ends) products of mouse bladder cDNA.

Example 2
Expression of a Fusion Gene (UPII-lacZ) in Transgenic Mice

A 6-kb XhoI DNA fragment of the G1 genomic clone (FIG. 1a) was subcloned in pGEM7Z and then restriction-cut to yield a 3.6-kb DNA fragment of G1 clone (extending from the XhoI site at −3.6 kb to the BamHI site at −42 bp relative to the transcription initiation site) and inserted into the SmaI site of a lacZ vector, placF, (Peschon et al. *Proc. Natl. Acad. Sci. USA* 1987, 84, 5316–5319; Mercer et al. *Neuron* 1991, 7, 703–716) to generate pUPII-LacZ (FIG. 3). The 7.1-kb fusion gene was excised using Kpn I and Hind III, gel-purified, and microinjected into fertilized mouse eggs (from F1 hybrids of C57BL/6J×DBA2), which were implanted into CD-1 foster mothers. The lacZ transgene was identified by Southern blot analysis of tail DNA in accordance with methods well known in the art. Positive founder animals were back-crossed with (C57BL/6J×DBA2) F1 hybrids to generate semizygous animals that were used for studying transgene expression.

Example 3
Production of a Mouse Model of Bladder Cancer

A chimeric gene was constructed using a 3.6 kb 5'-flanking sequence of mouse uroplakin II gene and a 2.8 kb SV40 large T oncogene in accordance with procedures described in Example 2. The resulting chimeric gene was microinjected into fertilized mouse eggs which were then implanted into foster mothers to generate transgenic mouse lines. Histological examination of tumors formed in these animals was performed to ascertain tumor cell type and invasiveness. Further, expression of SV40 large T oncogene in the tumors of these mice was confirmed by reverse transcriptase polymerase chain reaction.

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 3963
      (B) TYPE: Nucleic Acid
      (C) STRANDEDNESS: Single
      (D) TOPOLOGY: Linear (iv) ANTI-SENSE: No (xi) SEQUENCE DESCRIPTION: SEQ ID NO: 1:

```
GAGCTCAGGT CCTATCGAGT TCACCTAGCT GAGACACCCA CGCCCCTGCA          50

GCCACTTTGC AGTGACAAGC CTGAGTCTCA GGTTCTGCAT CTATAAAAAC         100

GAGTAGCCTT TCAGGAGGGC ATGCAGAGCC CCCTGGCCAG CGTCTAGAGG         150

AGAGGTGACT GAGTGGGGCC ATGTCACTCG TCCATGGCTG GAGAACCTCC         200

ATCAGTCTCC CAGTTAGCCT GGGGCAGGAG AGAACCAGAG GAGCTGTGGC         250

TGCTGATTGG ATGATTTACG TACCCAATCT GTTGTCCCAG GCATCGAACC         300

CCAGAGCGAC CTGCACACAT GCCACCGCTG CCCCGCCCTC CACCTCCTCT         350

GCTCCTGGTT ACAGGATTGT TTTGTCTTGA AGGGTTTTGT TGTTGCTACT         400

TTTTGCTTTG TTTTTTCTTT TTTAACATAA GGTTTCTCTG TGTAGCCCTA         450

GCTGTCCTGG AACTCACTCT GTAGACCAGG CTGGCCTCAA ACTCAGAAAT         500

CCACCTTCCT CCCAAGTGCT GGGATTAAAG GCATTCGCAC CATCGCCCAG         550

CCCCCGGTCT TGTTTCCTAA GGTTTTCCTG CTTTACTCGC TACCCGTTGC         600

ACAACCGCTT GCTGTCCAAG TCTGTTTGTA TCTACTCCAC CGCCCACTAG         650

CCTTGCTGGA CTGGACCTAC GTTTACCTGG AAGCCTTCAC TAACTTCCCT         700

TGTCTCCACC TTCTGGAGAA ATCTGAAGGC TCACACTGAT ACCCTCCGCT         750

TCTCCCAGAG TCGCAGTTTC TTAGGCCTCA GTTAAATACC AGAATTGGAT         800

CTCAGGCTCT GCTATCCCCA CCCTACCTAA CCAACCCCCT CCTCTCCCAT         850
```

-continued

| | |
|---|---|
| CCTTACTAGC CAAAGCCCTT TCAACCCTTG GGGCTTTTCC TACACCTACA | 900 |
| CACCAGGGCA ATTTTAGAAC TCATGGCTCT CCTAGAAAAC GCCTACCTCC | 950 |
| TTGGAGACTG ACCCTCTACA GTCCAGGAGG CAGACACTCA GACAGAGGAA | 1000 |
| CTCTGTCCTT CAGTCGCGGG AGTTCCAGAA AGAGCCATAC TCCCCTGCAG | 1050 |
| AGCTAACTAA GCTGCCAGGA CCCAGCCAGA GCATCCCCCT TTAGCCGAGG | 1100 |
| GCCAGCTCCC CAGAATGAAA AACCTGTCTG GGGCCCCTCC CTGAGGCTAC | 1150 |
| AGTCGCCAAG GGGCAAGTTG GACTGGATTC CCAGCAGCCC CTCCCACTCC | 1200 |
| GAGACAAAAT CAGCTACCCT GGGGCAGGCC TCATTGGCCC CAGGAAACCC | 1250 |
| CAGCCTGTCA GCACCTGTTC CAGGATCCAG TCCCAGCGCA GTATGGCATC | 1300 |
| CACACTGCCT GTCCAGACCT TGCCCCTGAT CCTGATTCTG CTGGCTGTCC | 1350 |
| TGGCTCCGGG GACTGCAGGT CTCTATTGCT GGTGGGTGCG AGGAGGGTTT | 1400 |
| CAGAGCGCTA GACAGGGAAC ATTGTCTCCC CAGGGCTCTC AAGGACAGGA | 1450 |
| ATGTTGGTCT AGCTGGTTGG GGTTGAGAGT TACTAGTGGT AGGAATCAGG | 1500 |
| TGACAAATTC CTGGGCTTCT TCCCAGATCC AGGAGTCAAG AAATTTGGGT | 1550 |
| AAGTGTCCAA GGTTTGTGTG AGTTGGGCGA GACTGGGGAC TGACTGGGTG | 1600 |
| CCATGGTCTA GTTTGGGTCG GTAGGGCTAT CTGGCTCCCA ACAGCGCGGC | 1650 |
| GTACCCACCA TCTGCAGATC AAGCCTGCCA TCTGGTGGTC AGATCCACAC | 1700 |
| GCTCCTCTTC TGTCTCTGCA CCCTTAGCAA TGACCACCCA CCCACCCCGC | 1750 |
| CAGCTCTGAG TTAAGAGGGG GCTAACTCCT GAGTTCCCTC TCGGCTCCCT | 1800 |
| AACAGACTTC AACATCTCAA GCCTCTCTGG TCTGCTGTCT CCGGCGCTAA | 1850 |
| CAGAAAGCCT GTTAATTGCC TTGCCCCCAT GTCACCTCAC GGGAGGTAAT | 1900 |
| GCCACATTGA TGGTCCGGAG AGCCAACGAC AGCAAAGGTA GACCTCCCTT | 1950 |
| GTACCCATTT ATTCTACTCG TCGTAACCCC TCTTAACGAT ACCCAAGAGC | 2000 |
| TGCCCGTTCT ACAAGAGTGG ACGCTAGAAT CTGATCTTGC CTTTCACTCC | 2050 |
| TATTTCCCCT CAGTGGTTAA GTCAGACTTT GTGGTGCCTC CATGTCGCGG | 2100 |
| GCGCAGGGAG CTTGTGAGCG TGGTGGACAG TGGGTCTGGC TACACCGTCA | 2150 |
| CAAGGCTCAG CGCATATCAG GTGACAAACC TAACACCAGG AACCAAATAC | 2200 |
| TAGTAGGTAC CGATGGACAC CTGTGGAGGT GGGATGGCAA AAAAGGGAAG | 2250 |
| TGGAGGTCCC GTGAGGGTGG GGAAGTGCCG GGAAGCATGA GTTAGAGAGG | 2300 |
| GCACAGCTAA AGGGTAGGAA ATGTGAACCT GGACCCCAGG AGGGCCCAGA | 2350 |
| TGGGACACAT AGCTAGAAGG TGGAGGCTGG AACCCCTCCT CCCGAGTGCC | 2400 |
| AGATACGTAC AACCTCTGCT TTCTCTCAAC TCCGCCTCTA AAGCATATCC | 2450 |
| TACCGAGTAC AGAAGGGGAC GTCGACCGAG TCCAGTCCAG AGACTCCCAT | 2500 |
| GTCCACGCTT CCTCGTTAAG TAAAATGCCC GTCTCTCACA CTTCCCTAAG | 2550 |
| CTCCGACTTT TTTCTCCTAG AGCAAGTTAG CTAAACTGTT TCCCGAGTGC | 2600 |
| TCAGTCGCAC ACACACCCCC TCCCCAACCC CCCAGTATTT GGTATGGCCC | 2650 |
| CTCCTGTCCT GTTCAATCAT CTCTGCACTA GAGGTTCCTT GTGCAGAGGG | 2700 |
| ATGATGTCCT CCTTGGTGGC TCCTAAGTGT TGCTGTGAGG GGGGTCTATG | 2750 |
| TTTGCTTGAC TGGTTGGCTG GATGACCAGT TGAACTGATG CTGGAGGCTA | 2800 |
| CTGGATGGCT GGGCTAATGC TGTGAACCAC AGGAGCTACC TAGGAACCCC | 2850 |

```
                                                                  -continued

TTCAACTCAC AGAGGTTCCC CCATCTTCTT CTGACAGGAA AAAACATGGA                  2900

GTCTATTGGG TTAGGAATGG CCCGGACAGG AGGGATGGTG GTCATCACAG                  2950

TGCTGCTGTC TGTGGCCATG TTCCTGTTGG TCGTGGGTCT TATTGTTGCC                  3000

CTGCACTGGG ATGCCCGCAA ATGAAAAGGG CTCTCCTGCA TCCCAGGCTC                  3050

CTCCAAGAAG TCCAGCCTGC CTCCTGCCAG GCTGTAGTCA CTGGCTTCTC                  3100

AGTGGCTTTT CTTCCCTCTC CCCGCCCCCT CCTCGAGTCC ACTCCTGACA                  3150

GTGCCCCCTC CCTGCTCCCT GTCTCACCTT GCAGCACTCC CTGCTAGCCC                  3200

CACTGCAATC CTGCCAACAC TGATTTATCT CTTAACTGTA CTTAATTCTC                  3250

ACAATAAAGG CTGACCCACG TAGTATGTCT CATCTCCGAC CATGTCTATG                  3300

TGAGTCACCC CTTTAGCTGG TCCCCTTATG CACATATCAA AACTACCAAT                  3350

GTCAAGGTCA CGTGCATGTC ATTTTCTCTA TCCCAAACCC CAAGGGTGAC                  3400

TTTTACCAGG AGGGAGGCAA GCAGAGGCAG AGATAATGAA GCCTCAAGCC                  3450

CAGACTAGGG AAGCCCTCCA AGCCCCAGAC CTAGGGCTTG GGTTTTGCAT                  3500

CCTGCACTCA GTAGATACCC AAGCAGGAGT CTAGTTGGGC AGGGGGTAGA                  3550

AGCTGGATCA CCATGTGAGC CTGACTGGGA AGCTGACAGA ACTAGGGAAG                  3600

AACTAGAGAA AACACAAACA GGGCAGGCCC TCCAGCCCTG GGTGAAGAAC                  3650

ATGCTAAACG GTTCTAGACC CCTAGAGCCG AGGTGGACGG AAGCTCCTGG                  3700

AAGGGGGAGG GGGGACACA ACATAGGTAA ACAGGCAGTG GCACCCTCGT                   3750

CCATTTTTAA AATATAGTTT TGTTCTATAA AAGTTTTATT TATTTATTTA                  3800

TTTGCTTGTT TTTATTTGTT TGTTTGTTTT CCAGAGCTGA GGCAAAAACC                  3850

CAGGACCTTG AGCTTGCTAG GCAAGTGCTC TACCACTGAG CTAAATCCCC                  3900

AACCCCTGTT TTTGTTTTTT TGAAGCAGGG TTTCTCTGTG TAGCTCTGGC                  3950

TGTCCTAGAG CTC                                                         3963

(2) INFORMATION FOR SEQ ID NO: 2:

(i) SEQUENCE CHARACTERISTICS:
        (A) LENGTH: 11
        (B) TYPE: Amino Acid
        (D) TOPOLOGY: Linear (xi) SEQUENCE DESCRIPTION: SEQ ID NO: 2:

GLU LEU VAL SER VAL VAL ASP SER GLY SER GLY
1               5                   10
```

What is claimed is:

1. A vector comprising a promoter construct linked to a heterologous DNA encoding a selected biologically active molecule, wherein said promoter construct directs expression of the heterologous DNA to the urothelium so that the selected biologically active molecule expressed by said heterologous DNA is detected in urine.

2. The vector according to claim 1, wherein said promoter construct is a UPIa promoter.

3. The vector according to claim 1, wherein said promoter construct is a UPIII promoter.

4. The vector according to claim 1, wherein said promoter construct is a urohingin promoter.

5. A method of producing a selected biologically active molecule in urine of a non-human mammalian animal comprising:

(a) generating a nonhuman transgenic mammalian animal comprising a promoter construct linked to a heterologous DNA encoding a selected biologically active molecule, wherein said promoter construct directs expression of the heterologous DNA to the urothelium so that the selected biologically active molecule expressed by said heterologous DNA is detected in urine;

(b) expressing the heterologous DNA in the nonhuman transgenic mammalian animal so that the biologically active molecule is produced in urothelial tissue of said animal; and (c) recovering detectable levels of the selected biologically active molecule in urine produced by the nonhuman transgenic mammalian animal.

6. The method according to claim 5, wherein said transgenic mammalian animal is selected from the group consisting of mice, rats, cows, pigs, sheep, goats, monkeys, and rabbits.

7. A nonhuman transgenic mammalian animal whose genome comprises a promoter construct linked to a heterologous DNA encoding a selected biologically active molecule, wherein said promoter construct directs expression of the heterologous DNA to the urothelium and said transgenic mammalian animal has detectable levels of said selected biologically active molecule in its urine.

8. The nonhuman transgenic mammalian animal according to claim 7 which is selected from the group consisting of mice, rats, cows, pigs, sheep, goats, monkeys, and rabbits.

* * * * *

UNITED STATES PATENT AND TRADEMARK OFFICE
CERTIFICATE OF CORRECTION

PATENT NO. : 6,339,183 B1
DATED : January 15, 2002
INVENTOR(S) : Tung-Tien Sun

It is certified that error appears in the above-identified patent and that said Letters Patent is hereby corrected as shown below:

Column 1,
Line 13, before "BACKGROUND OF THE INVENTION", insert the following new section:
-- GOVERNMENT LICENSE RIGHTS
 The U.S. Government has a paid-up license in this invention and the right in limited circumstances to require the patent owner to license others on reasonable terms as provided for by the terms of Contract No. DK039753 and DK049469 awarded by the National Institutes of Health of the U.S. Department of Health and Human Services. --

Signed and Sealed this

Twenty-first Day of June, 2005

JON W. DUDAS
*Director of the United States Patent and Trademark Office*